(12) United States Patent
Klootz (10) Patent No.: US 6,224,227 B1
(45) Date of Patent: May 1, 2001

(54) SURGICAL HEADLIGHT ASSEMBLY WITH DETACHABLE VIDEO-CAMERA MODULE

(76) Inventor: Jack Klootz, 82 Erin Way, Naples, FL (US) 34119

( * ) Notice: Subject to any disclaimer, the term of this patent is extended or adjusted under 35 U.S.C. 154(b) by 0 days.

(21) Appl. No.: 09/421,991

(22) Filed: Oct. 20, 1999

(51) Int. Cl.[7] .................................................. F21V 21/084
(52) U.S. Cl. ........................ 362/105; 362/572; 348/370
(58) Field of Search .................... 362/570, 572, 362/575, 105, 16, 8, 804; 600/249

(56) References Cited

U.S. PATENT DOCUMENTS

| | | | |
|---|---|---|---|
| 4,616,257 | * 10/1986 | Kloots ................................... | 348/370 |
| 4,797,736 | * 1/1989 | Kloots ................................... | 348/370 |
| 6,120,161 | * 9/2000 | Van Der Bel ......................... | 362/105 |

* cited by examiner

Primary Examiner—Sandra O'Shea
Assistant Examiner—Hargobind S. Sawhney (74) Attorney, Agent, or Firm—Malin, Haley & DiMaggio, P.A.

(57) ABSTRACT

An improved surgical headlight assembly having a detachable video camera module. The present invention allows viewers at a remote location to observe an operation procedure on a video monitor from a surgeon's visual perspective. The headlight assembly which is secured via a headband placed around the surgeon's forehead, receives light from a light source via a fiber optic cable. The light is sufficient to illuminate the surgeon's area of operation. A video camera is removably affixed to the headlight assembly and, via the use of a roof prism residing within the video camera housing, deflects an erected and accurate image to the video camera, which in turn, transmits the image to a remote video monitor via a coaxial communications cable. A microphone may be provided to allow the surgeon to provide verbal comments to the viewers observing the procedure. The direction of the beam exiting the headlight assembly may be manually adjusted to insure that the beam of light illuminates the area within the focal point of the viewing lens within the video camera. The entire headlight-video camera assembly rests comfortably between the eyes of the surgeon thereby allowing the surgeon to perform the medical procedure in an unhindered manner.

10 Claims, 6 Drawing Sheets

SURGICAL HEADLIGHT ASSEMBLY WITH DETACHABLE VIDEO-CAMERA MODULE

BACKGROUND OF THE INVENTION

1. Field of the Invention

This invention relates to a surgical headlight that provides illumination to a surgeon's area of work, and specifically to a surgical headlight having a detachable video camera module that allows for videotaping of the surgical area and transmitting of the video to a remote video monitor where a viewer can witness the surgical area as seen from the surgeon's perspective.

2. Description of Related Art

The use of illuminating headlights to provide illumination to a surgical area is well known in the prior art.

U.S. Pat. No. 4,616,257 issued to Kloots, et al, shows a head mounted illuminating apparatus including video and audio transmittal means. This patent uses a fiber optic cable to provide light to an illumination lens and a communication cable to receive images through a video lens and to provide images to a remote video monitor. A light-to-electrical transducer in the form of an integrated circuit chip converts light images, which strike upon the surfaces of the chip, and converts them to electrical signals that are removed by the communications cable to a remote video monitor screen. However, a drawback of this invention is the fact that the module which houses the video lens is not separable from the module housing the illumination lens. Further, the use of a transducer may not be cost effective or may not accurately convert the light images to clear, accurate images as seen by viewers at remote locations. Further, the modules housing the respective lenses are somewhat bulky and situated at angles, which may be inhibitive to the surgeon while performing the operation.

U.S. Pat. No. 4,516,190 issued to Kloots, describes a surgical headlamp that is removably mounted to a headband and that utilizes a remote light source transmitted via a fiber optic cable. However, the apparatus described in this patent maintains a fixed 90° angle between the entering light and the exiting beam through the illuminating lens. Further, there is no video means to record, in a real time manner, the images viewed by the surgeon. In the medical arena, it is essential that a surgeon perform his work with a fully illuminated working area. With the advent of fiber optics it is now common to supply light via a fiber optic cable to a module which houses an illumination lens, whereby the light passing through the lens forms a beam which can illuminate the surgeon's entire work area.

Because the beam exits the headlight assembly in the same direction as the surgeon's line of sight, the surgeon can simply turn his head and the beam follows. It is also desirable to have the surgeon's work viewed by others, such as medical students, in real time, as the surgeon is going through the steps of his operation procedure. However, due to the fact that video cameras may obstruct the surgeon's views, most cameras are placed at a remote location. However, this provides students with a view different than what the surgeon actually sees. In complicated surgical procedures, it would be advantageous for students to view the surgery from the same perspective as the surgeon. It would also be desirable to include a microphone near the surgeon's mouth to allow those viewing the operation to also listen to verbal comments and instructions from the surgeon.

Large, bulky headlight-camera assemblies may prove to be an annoyance to the surgeon who needs absolute concentration without distraction. Therefore, the headlight assembly must be small, light, and unobtrusive.

Students viewing the procedure at a remote video monitor must be provided with accurate images as they may be performing the very same procedure at a later date. Needless to say any imperfection in the image displayed on the monitor, however minute, may lead to a monumental error. It is therefore essential that the image, as seen by the surgeon, be reproduced clearly and accurately.

Therefore, it is an object of the invention to provide a headlight assembly affixed to the surgeon's head via a headband, which illuminates the working area while not obstructing the surgeon's line of sight.

It is a further object of this invention to provide a video camera affixed to the headlight to allow remote viewers to witness the actual observations of the surgeon, from the surgeon's viewing perspective.

It is still another object of this invention to provide a headlight module where the video camera is detachable from the headlight assembly, thereby allowing each to be used independently of the other.

A still further object of this invention is to provide a surgical headlight assembly having a detachable video camera module wherein the assembly and module are located directly between the surgeon's eyes therefore not inhibiting the surgeon's view.

It is yet still another object of this invention to provide a surgical headlight assembly having a detachable video camera module wherein a prism is situated within the video camera module to provide an accurate reflection of the object viewed by the surgeon, to a remote viewer.

It is yet another object of this invention to provide a roof prism situated within the video camera module whereby the object viewed by the surgeon is clearly and accurately refracted through the prism along the communications cable to be viewed at a remote site.

It is yet another object of the invention to provide a surgical headlight assembly having a greater than 90° angle between the entry of light via the fiber optic cable and the direction of the light beam through the illumination lens.

Thus, the prior art shows surgical headlamp devices with and without video cameras mounted thereon, wherein the video lens module and the illumination lens module are bulky, rigid and use image-reproduction circuitry that may not accurately reproduce the actual image as seen by the surgeon.

The present invention overcomes problems shown in the prior art.

BRIEF SUMMARY OF THE INVENTION

The present invention relates to an improved surgical headlight assembly having a detachable video camera module to allow remote viewers to witness the image seen by a surgeon during the performance of an operation or other medical procedure, from the surgeon's perspective.

The system includes: a headband designed to fit around the forehead of a human being; a first housing including a barrel section and an illumination system; a second housing detachably mounted to the first housing; a video camera having a viewing lens situated within the second housing; a detachable fiber optic cable extending from the top of the first housing wherein the fiber optic cable provides light to the illumination system such that said light passes through the illumination lens and produces a beam of light sufficient in size to illuminate a surgeon's operating area; a coaxial communications cable connected at its first end to the video camera and at its second end to a video monitor. An important feature provided by Applicant's invention is the use of a prism mounted within the second housing. The prism deflects the image, as seen by the surgeon, to the video camera wherein the video camera transmits the image to the video monitor via the communications cable.

In the preferred embodiment, the prism is a roof prism comprising a 90° total internal reflection (TIR) roof, which deflects the image seen by the surgeon through an angle of 90°. The roof prism, or KLOOTZ-AMICI™ prism is a right angle prism wherein the hypotenuse has been replaced by a 90° total internal reflection (TIR) roof. Glass that does not contribute to the clear aperture is trimmed away to reduce the size and the weight of the prism.

The KLOOTZ-AMICI™ prism allows for image erection and angle deflection, in order to allow a viewer at a remote site to witness, via the video monitor, an erected image that is an exact reproduction of the image witnessed by the surgeon.

The illumination system of the headlight assembly further includes an illumination lens and a mirror situated within said first housing wherein the mirror is at a substantially 45° angle with respect to the illumination lens. It is in this configuration that the beam of light exits the illumination lens of the headlight assembly at a substantially 90° angle with respect to the axis of entry of the light into the first housing, transmitted by the fiber optic cable.

In an alternate embodiment, the mirror is at a substantially 60° angle with respect to the illumination lens. In this configuration, the beam of light exiting the illumination lens is at a substantially 105° angle from the axis of entry of the light transmitted by the fiber optic cable.

The improved headlight assembly is designed such that the center lines of the illumination lens and the viewing lens lie in a vertical plane midway between the surgeon's eyes. Therefore, the surgeon's eyes are not blocked and the surgeon is not distracted and may carry on his procedure as if the headlight assembly was not present.

The surgeon can position the headlight assembly to his or her liking by utilizing connecting means in the form of a rotating bracket. The bracket rotatably connects the headband to the first housing of the headlight assembly, thereby allowing the first housing and the second housing to be rotated along each of their vertical axes in order to allow the surgeon to properly position the headlight assembly in front of the object being viewed.

A key feature of the improved headlight assembly of the present invention is its relatively small size and light weight. The headlight assembly, including the video camera weighs approximately 100 grams. The first housing, including the barrel section is approximately 1.42 inches wide and 2.36 inches in length.

It should be noted that the video camera is completely detachable from its housing thereby allowing the headlight portion of the headlight assembly to be used without the video camera. This may be necessary if the patient refuses to allow their procedure to be video-taped, or if the surgeon chooses not to have the procedure viewed. After the video camera is detached, the headlight assembly becomes a headlight, which provides a large illumination area to he surgeon's field of work.

With the video camera in place, light enters the first housing via the fiber optic cable, is deflected by the mirror positioned within the illumination system, and a beam of light is emitted through the illumination lens wherein the focal point of the viewing lens of the video camera lies within the beam emitted by the illumination lens.

In accordance with these and other objects which will become apparent hereinafter, the instant invention will now be described with particular reference to the accompanying drawings.

DETAILED DESCRIPTION OF THE INVENTION

Figure 1:
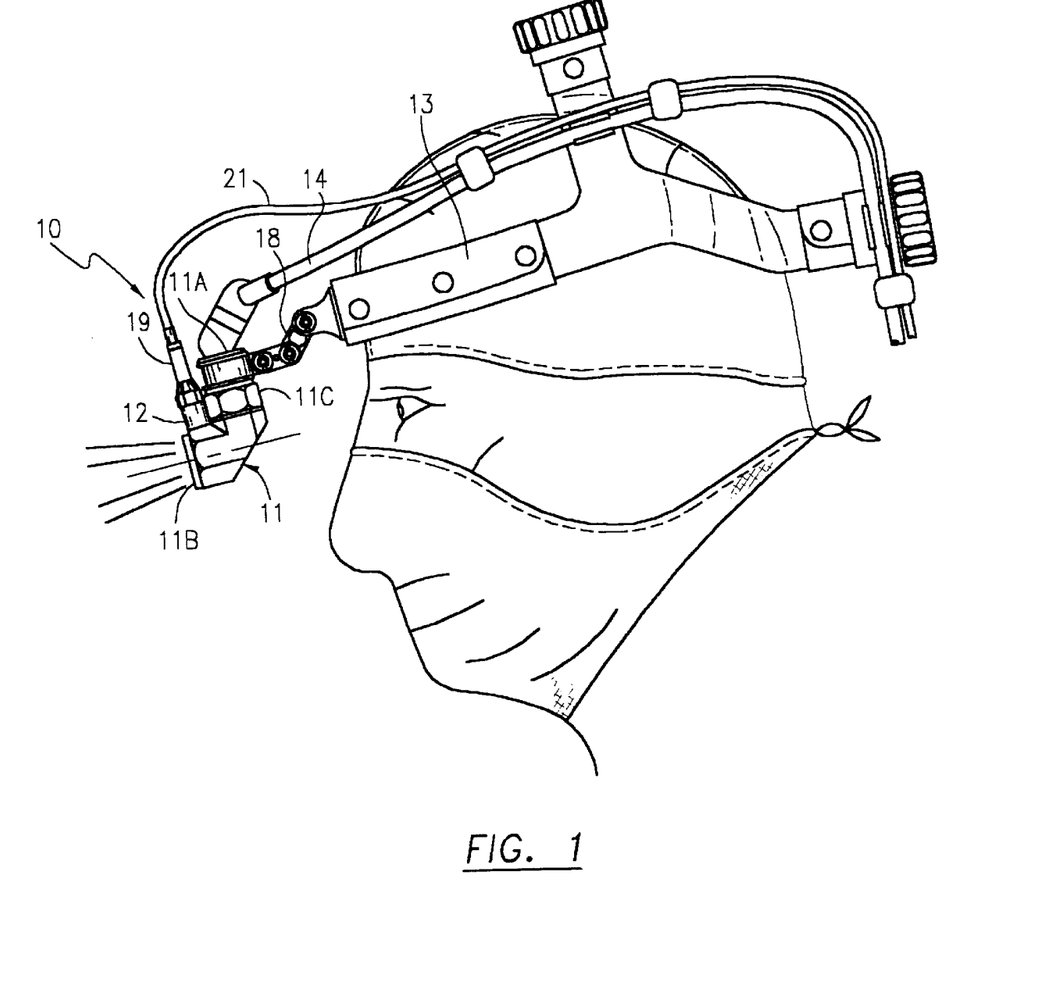
FIG. 1 is a side view of the improved headlight assembly and detachable video camera of the present invention.

Turning now to the drawings, FIG. 1 schematically illustrates the improved surgical headlight assembly of the present invention. The headlight assembly, shown generally as reference numeral 10, includes a first housing 11, and a second housing 12 rotatably affixed to a headband 13, which is placed around a user's forehead.

First housing 11 has a top end 11A and a bottom end 11B, at a substantially right angle with respect to top end 11A, wherein a detachable fiber optic cable 14 is connected to top end 11A of first housing 11. Fiber optic cable 14 carries light from a remote source to first housing 11. First housing and the illumination system therein, is described in U.S. Pat. No. 4,616,257 issued on May 7, 1985, to Kloots et al., and is incorporated herein by reference.

Figure 2:
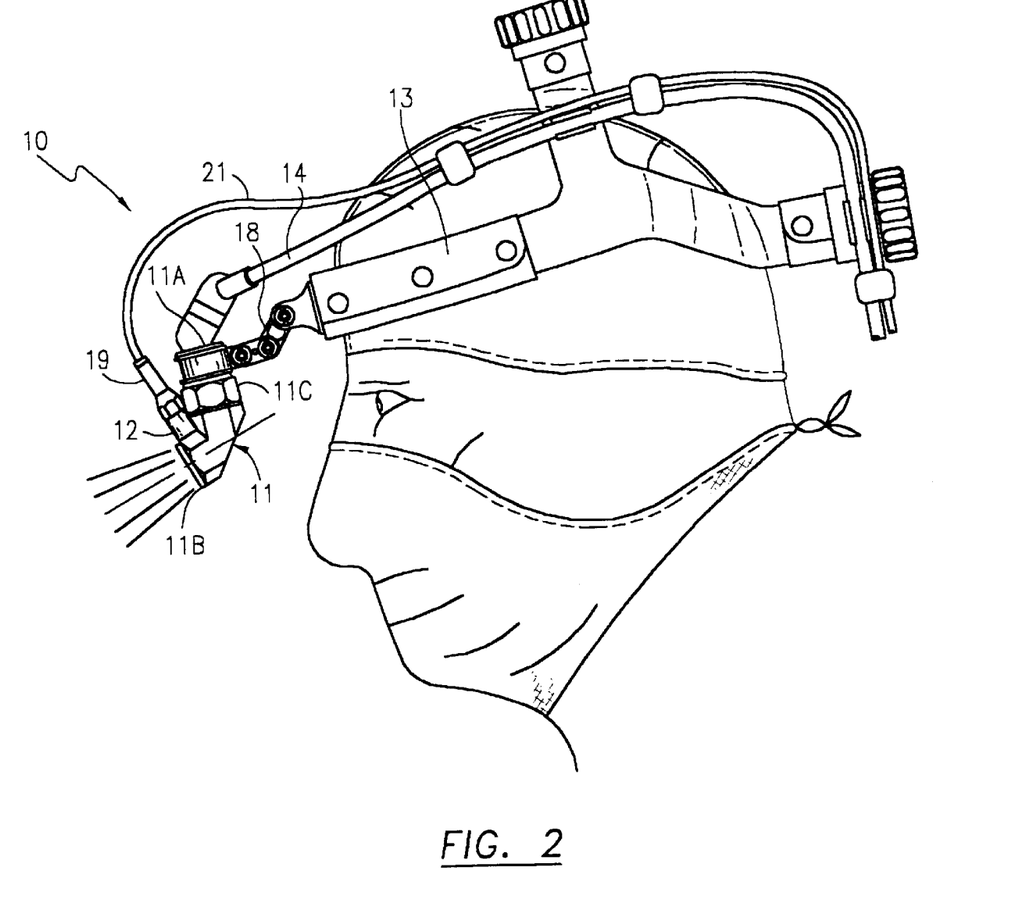
FIG. 2 is a side view of an alternate embodiment of the improved headlight assembly and detachable video camera of the present invention.

FIG. 2 shows an alternate embodiment of headlight assembly 10, wherein top end 11A is in a substantially 105° relationship with bottom end 11B.

Figure 3:
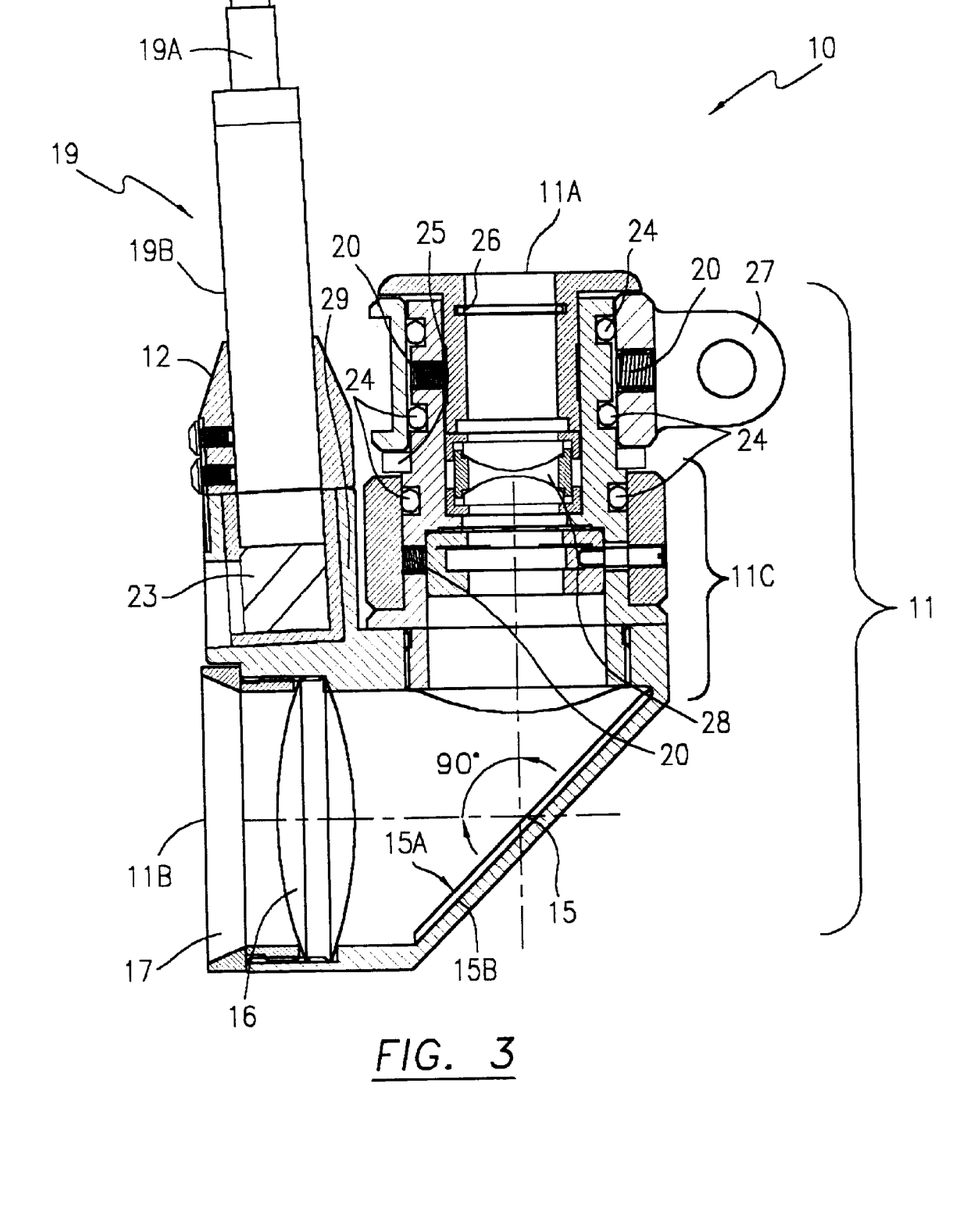
FIG. 3 is a side cut-away view of the present invention depicting the second housing containing the video camera detachably mounted to the first housing which contains the illumination system.

FIG. 3 shows a cut-away view of first housing 11 and second housing 12. First housing 11 includes a central barrel portion 11C. First housing 11 includes a plurality of screws 20, a plurality of O-rings 24, a washer 25, a spring 26, and a connecting ring 27, which connects headlight assembly 10 to headband 13. A condenser lens assembly 28 resides within barrel portion 11C of first housing 11.

In the preferred embodiment of the invention, the horizontal axis of second end 11B of first housing 11 is at a substantially 90° angle with respect to the vertical axis of top end 11A of first housing 11. Front surface mirror 15 resides within first housing 11. An illumination lens 16 also resides within first housing 11 proximate bottom end 11B. A retaining ring 17 is situated between second end 11B and illumination lens 16.

Light is carried to first housing 11 via fiber optic cable 14 as seen in FIG. 1. Light arrives at top end 11A of first housing 11 and travels downwards through barrel portion 11C until the light strikes upon the front surface 15A of mirror 15. Mirror 15 rests on mirror supporting wall 15B which has a thickness of approximately 0.5 inches.

In the preferred embodiment of the present invention, shown in FIG. 3, the light entering top end 11A is deflected 90° until it travels through illumination lens 16 and exits through second end 11B of first housing 11. As the light passes through illumination lens 16, a beam of light is formed that illuminates an area in front of the user. Adjusting a bracket 18 seen in FIGS. 1 and 2, allows the user to easily raise or lower assembly 10, thereby altering the orientation of the projection of light, which may change the direction of the beam. This adjustment alters the vertical orientation of first housing 11, thereby changing the direction of the illumination beam.

FIG. 3 also shows a video camera 19 contained within a second housing 12. Video camera 19 has a diameter of approximately 7 mm and a length of approximately 47 mm. Second housing 12 is detachably mounted to first housing 11. In FIG. 3, video camera 19 is substantially vertical. However, in an alternate embodiment shown in FIG. 6, video camera 19 is at an angle with respect to first housing 11, taking into account the angled lower portion of first housing 11. In either embodiment, second housing 12 can be simply snapped into or out of a receiving notch 29 situated along the outer portion of first housing 11.

Figure 7A:
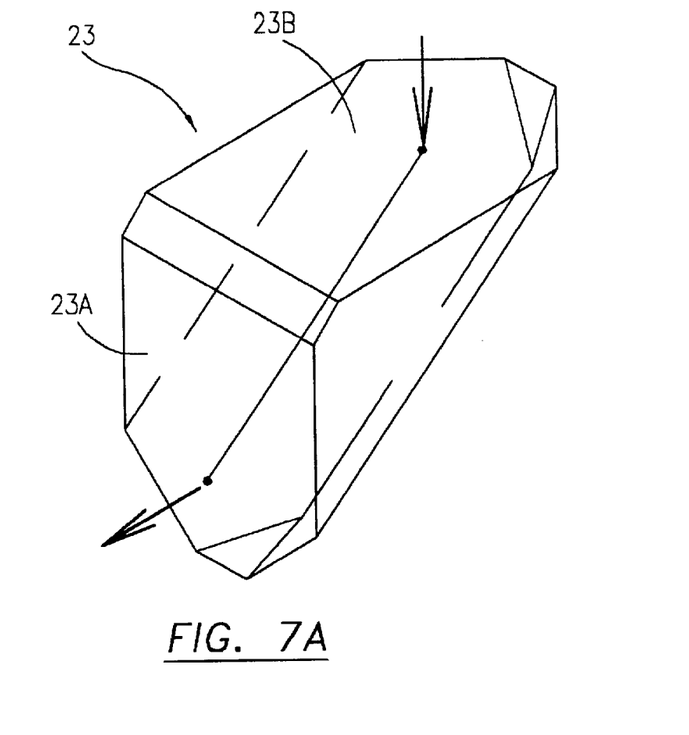
FIG. 7A shows a top perspective view of the KLOOTZ-AMICI™ roof prism utilized in the present invention.
Figure 7B:
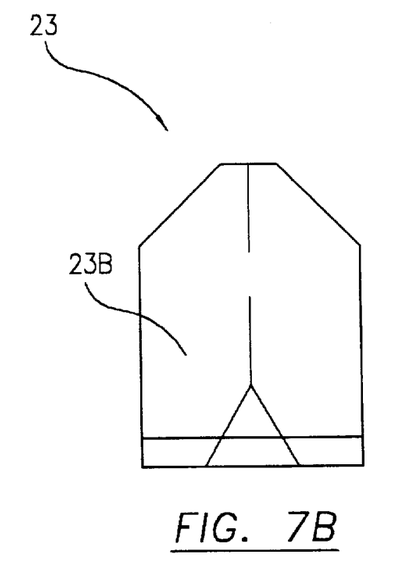
FIG. 7B shows a top view of the KLOOTZ-AMICI™ roof prism of FIG. 7A.
Figure 7C:
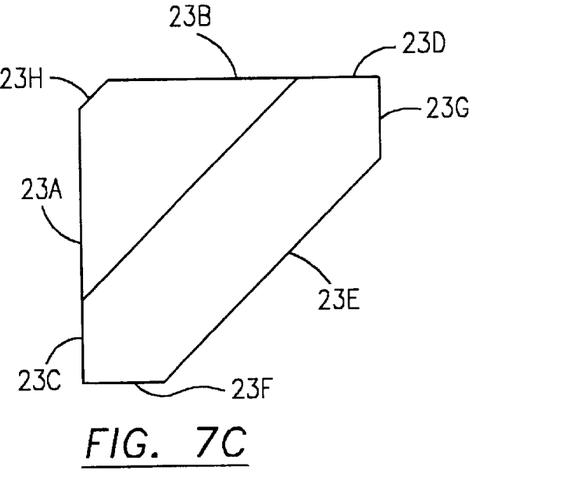
FIG. 7C shows a side view of the KLOOTZ-AMICI™ roof prism of FIG. 7A.

FIG. 3 shows prism 23 in a side view, within video camera 19. FIGS. 7A–7C show several views of prism 23. An image enters front face 23A of prism 23 and is both refracted and erected to exit through the rear face 23B of prism 23. This is the image that is refracted 90 degrees upwards by prism 23 through objective video lens 22 (shown in FIG. 4) and processed by video camera 19. This image is then transported, via communications cable 21, to a video monitor (not shown) at a remote site to be witnessed by, for example, medical students wishing to observe a medical procedure. The orientation of prism 23 within video camera 19 is critical as the angles of the prism's faces must direct the image through the video camera 19.

Figure 4:
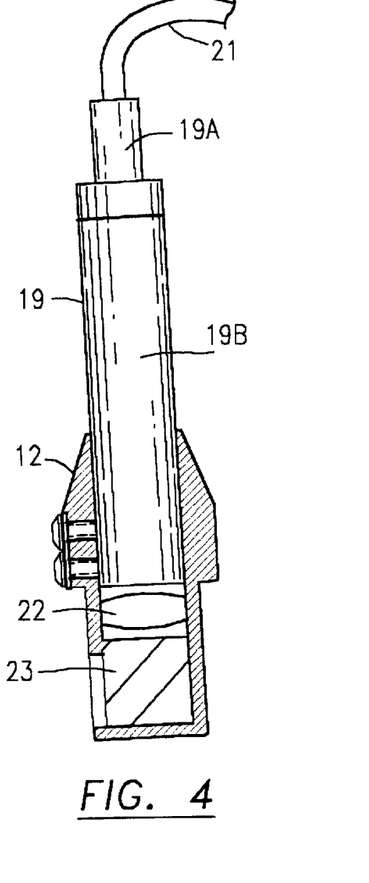
FIG. 4 shows a side view of the second housing containing the video camera completely detached from the first housing.

FIG. 4 shows video camera 19 and second housing 12 completely detached from first housing 11. Video camera 19 is comprised of a top elongated portion 19A which receives one end of a communications cable 21. Video lens 22 is situated toward the bottom of video camera 19. The bottom portion 19B of video camera 19 houses prism 23 which deflects the image seen by the user.

Figure 5:
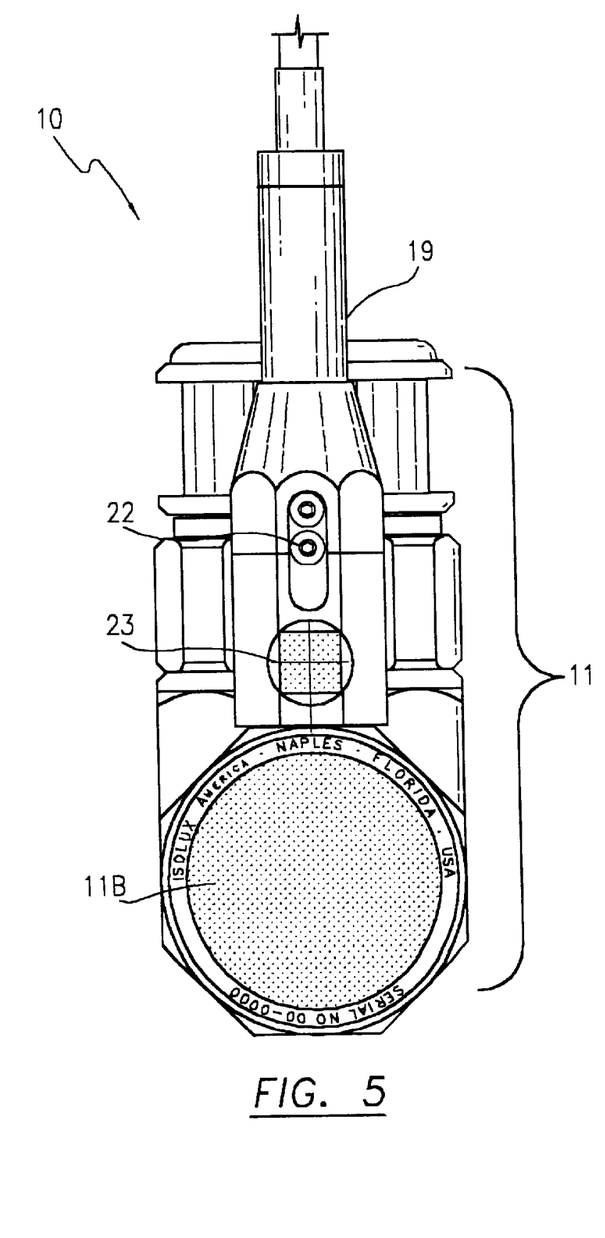
FIG. 5 shows a front view of the headlight assembly and detachable video camera of the present invention.

FIG. 5 shows a front view of headlight assembly 10. Second end 11B can be seen directly below and in vertical alignment with video lens 22 and prism 23. It is evident from this view, that because second end 11B of first housing 11 which houses illumination lens 16, is in vertical alignment with prism 23, the image witnessed by the user can be illuminated and refracted to video camera 19, and ultimately to a remote video monitor, without the user's view being obstructed. The design of headlight assembly 10 is such that its narrow, elongated configuration does not interfere with the user's line of sight. Assembly 10 rests between the eyes of the user, allowing the user to operate without distraction.

Figure 6:
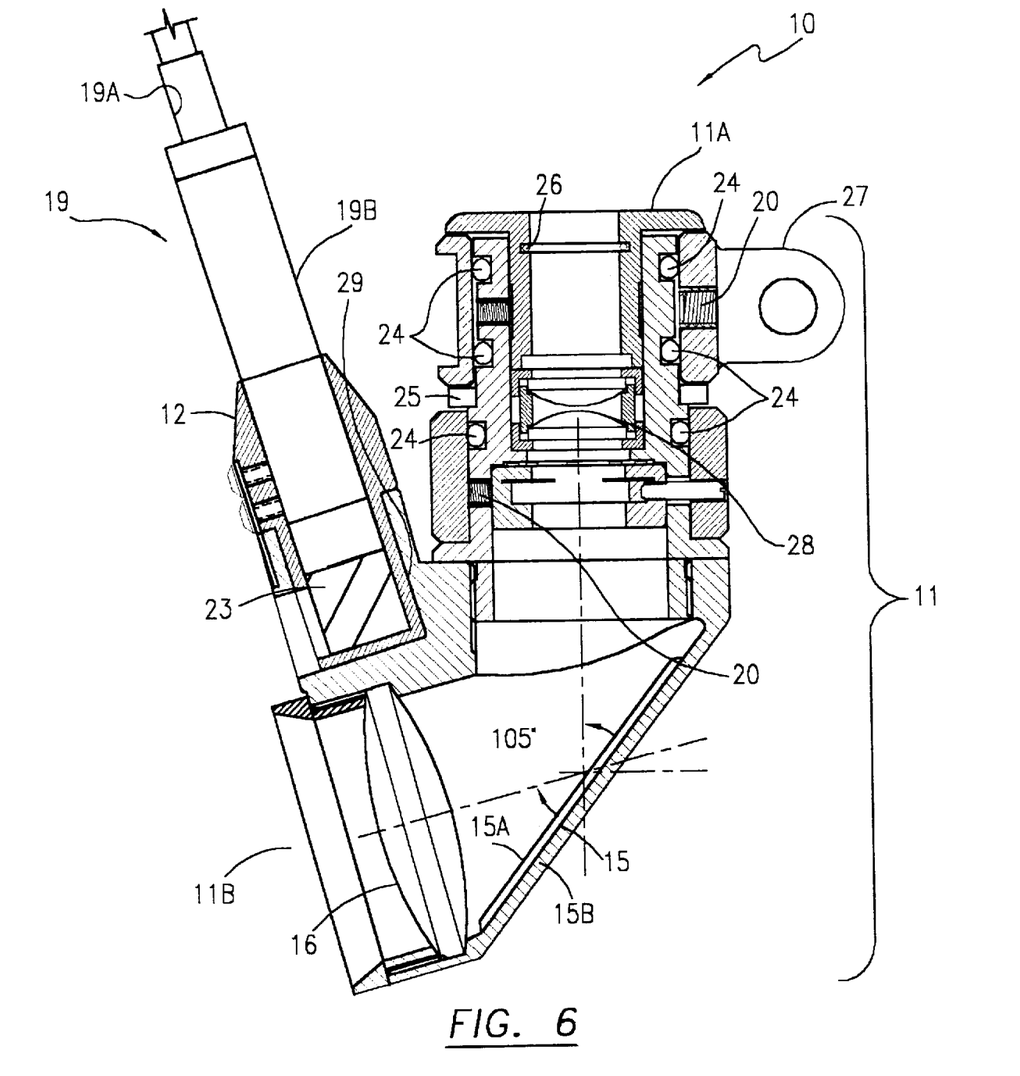
FIG. 6 shows a side cut-away view of an alternate embodiment of the present invention.

FIG. 6 shows an alternate embodiment of the present invention wherein first housing 11 is designed such that light entering through first end 11A strikes illumination lens 16 and is deflected 105° until the light exits second end 11B. This alternate design allows for less adjustment of headlight assembly 10 by the user via bracket 18, as the illumination beam now exits second end 11B of first housing 11 at a lower angle than in the preferred embodiment. With this embodiment, the exiting beam of light is now directed at angle lower and closer to the operating table.

FIG. 7A shows a transparent perspective view of prism 23, while FIGS. 7B and 7C show a top view and side view, respectively, of prism 23.

Prism 23 is the critical feature and key improvement of Applicant's invention. Prism 23 is a roof prism, and more particularly, a KLOOTZ-AMICI™ right-angle prism having the dimensions of 5×5×5 mm, plus or minus 0.15 mm, wherein the hypotenuse of the prism is replaced by a 90° tir roof, having a tolerance of plus or minus 3 degrees. The advantage of a prism of this type is that it provides both right-angle deflection and image erection so that the incoming light representing the image is deflected 90° so that video camera 19 may receive it, and its image is erected, that is re-inverted, so that it is no longer inverted and appears at the video monitor as identical to the image seen by the user. The front face 23A of prism 23 includes an anti-reflection coating comprised of $MgF_2$ which prevents portions of the image being viewed from reflecting away from front face 23A.

Referring to FIG. 7C, which depicts prism 23 in a side view, front face 23A and lower front edge 23C have a combined length of approximately 5 mm plus or minus 0.15 mm. These dimensions are mirrored on the prism's opposite face, where rear face 23B and lower rear edge 23D also combine to measure approximately 5 mm plus or minus 0.15 mm. Bottom edge 23E measures approximately 7.07 mm across with a tolerance of 0.15 mm, while the distance from the top edge 23H to the bottom edge 23E is approximately 4.83 mm plus or minus 0.15 mm. Finally, the bottom edge 23E is in a 45 degree relationship with front face 23A and lower front edge 23C, as well as with rear face 23B and lower rear edge 23D.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An improved surgical headlight assembly including a detachable video camera module comprising:

a headband designed to fit around the forehead of a human being;

a first housing having an illumination system, said illumination system comprising an illumination lens and a mirror;

a second housing detachably mounted to said first housing;

a video camera module situated within said second housing, said video camera module including a viewing lens;

a detachable fiber optic cable extending from the top of said first housing wherein said fiber optic cable provides light to said illumination system such that said light passes through said illumination lens and produces a beam of light sufficient in size to illuminate a surgeon's operating area;

a communications cable connected at its first end to said video camera module and at its second end to a video monitor; and a prism mounted within said second housing, wherein said prism reproduces an image as seen by the surgeon to said video camera wherein said video camera transmits said image to said video monitor via said communications cable.

2. The headlight assembly of claim 1, wherein said prism is a roof prism, said roof prism comprising a 90° total internal reflection (TIR) roof which deflects said image through an angle of 90°.

3. The headlight assembly of claim 1, wherein said mirror is situated within said first housing at a substantially 45° angle with respect to said illumination lens.

4. The headlight assembly of claim 1, wherein said mirror is situated within said first housing at a substantially 60° angle with respect to said illumination lens.

5. The headlight assembly of claim 3, wherein said beam exits said illumination lens at a substantially 90° angle from the axis of entry of said light via said fiber optic cable.

6. The headlight assembly of claim 4, wherein said light passing through said illumination lens exits said illumination lens at a substantially 105° angle from the axis of entry of said light via said fiber optic cable.

7. The headlight assembly of claim 1, wherein the center lines of said illumination lens and said viewing lens lie in a vertical plane midway between the surgeon's eyes.

8. The headlight assembly of claim 1, further comprising connecting means to rotatably affix said headband to said first housing, wherein said connecting means allows said first housing and said second housing to be rotated along each of their vertical axes in order to allow said user to position said headlight assembly in front of the object being viewed by said surgeon.

9. The headlight assembly of claim 1, wherein said headlight assembly including said video camera module weighs approximately 100 grams.

10. The headlight assembly of claim 1, wherein the focal point of said viewing lens lies within said beam emitted by said illumination lens.

* * * * *